US006433863B1

(12) United States Patent
Weiss

(10) Patent No.: US 6,433,863 B1
(45) Date of Patent: Aug. 13, 2002

(54) COMBINATION BREATHALYZER AND EYE-SENSOR

(76) Inventor: Ronald Weiss, 2131 Wantagh Ave., Wantagh, NY (US) 11793

( * ) Notice: Subject to any disclaimer, the term of this patent is extended or adjusted under 35 U.S.C. 154(b) by 0 days.

(21) Appl. No.: 09/755,574

(22) Filed: Jan. 8, 2001

(51) Int. Cl.$^7$ .............................................. G01N 21/00

(52) U.S. Cl. ....................................................... 356/72

(58) Field of Search ........................... 356/72, 364, 437, 356/326, 439, 435; 340/5.51–5.55, 5.8, 576, 5.81–5.85, 439, 575, 632, 539, 573.1–573.4, 634; 434/321–322, 362, 350; 600/532, 345; 382/124, 232; 73/23.3, 23.35

(56) References Cited

U.S. PATENT DOCUMENTS 4,916,435 A * 4/1990 Fuller ....................... 340/573.4
6,198,996 B1 * 3/2001 Berstis ......................... 701/36

* cited by examiner

Primary Examiner—Frank G. Font
Assistant Examiner—Tu T. Nguyen
(74) Attorney, Agent, or Firm—Myron Amer PC

(57) ABSTRACT

Positioning, by the use of a unitary construction, a breathalyzer and retina/eye-scanner a distance apart from each other that corresponds to the typical distance separating an individual's mouth and eyes, so that there can be positioned only one individual's face adjacent the unitary construction preparatory to the use thereof, which minimizes the use of two individuals, one to provide a sober breath to the breathalyzer and the other to provide a bogus retina scan of the identification of the individual using the breathalyzer.

1 Claim, 4 Drawing Sheets

COMBINATION BREATHALYZER AND EYE-SENSOR

This invention relates to an alcohol detection device, one component of which is commonly referred to as a breathalyzer and is of a type used to administer a test to a motor vehicle operator to determine the presence or absence of possible alcohol intoxication and in particular to such a device with associated electronic circuitry to control the mode, operative or otherwise, of an ignition circuit of a vehicle's prime mover. The device is particularly intended for use on automobiles or other road user vehicles to prevent or at least limit use of the vehicle by alcoholically intoxicated drivers.

BACKGROUND OF THE INVENTION

Field of the Invention

It is well established that numerous traffic accidents involve and in particular are caused by drivers intoxicated by alcohol. To this end, there is described herein a device which will detect the presence or otherwise of alcohol and if "alcohol free" conditions are not present maintain an ignition circuit of a vehicle's prime move inoperative. Within this specification the term "alcohol free" is used to conveniently describe conditions where there is complete absence of alcohol and also conditions where alcohol may be present but at a level below a level at which appropriate authorities have deemed as being the maximum permissible alcohol level for an operator of a vehicle. Again, while this level may vary from one place to another, they are well established at least as regards road vehicles such as automobiles.

It is known however from accident investigations involving alcoholically intoxicated drivers, that it is a common ploy for an impaired driver to "trick" vehicle interlock systems by have a sober accomplice perform the breathalyzer test so that the impaired driver can operate the vehicle.

SUMMARY OF THE INVENTION

Broadly, it is an object of the present invention to provide a vehicle interlock system which positively identifies drivers and repeatedly re-tests and re-verifies identity initially and during the course of vehicle operation.

More particularly, it is an object to provide an operative combination of breathalyzer and a selected user-identifying means so as to contribute to use of the combination by only one individual whose identity is verified, all as will be better understood as the description proceeds.

BRIEF DESCRIPTION OF THE DRAWING

The description of the invention which follows, together with the accompanying drawings should not be construed as limiting the invention to the example shown and described, because those skilled in the art to which this invention appertains will be able to device other forms thereof within the ambit of the appended claims.

DESCRIPTION OF THE PREFERRED EMBODIMENT

The Breathalyzer Component

Figure 2:
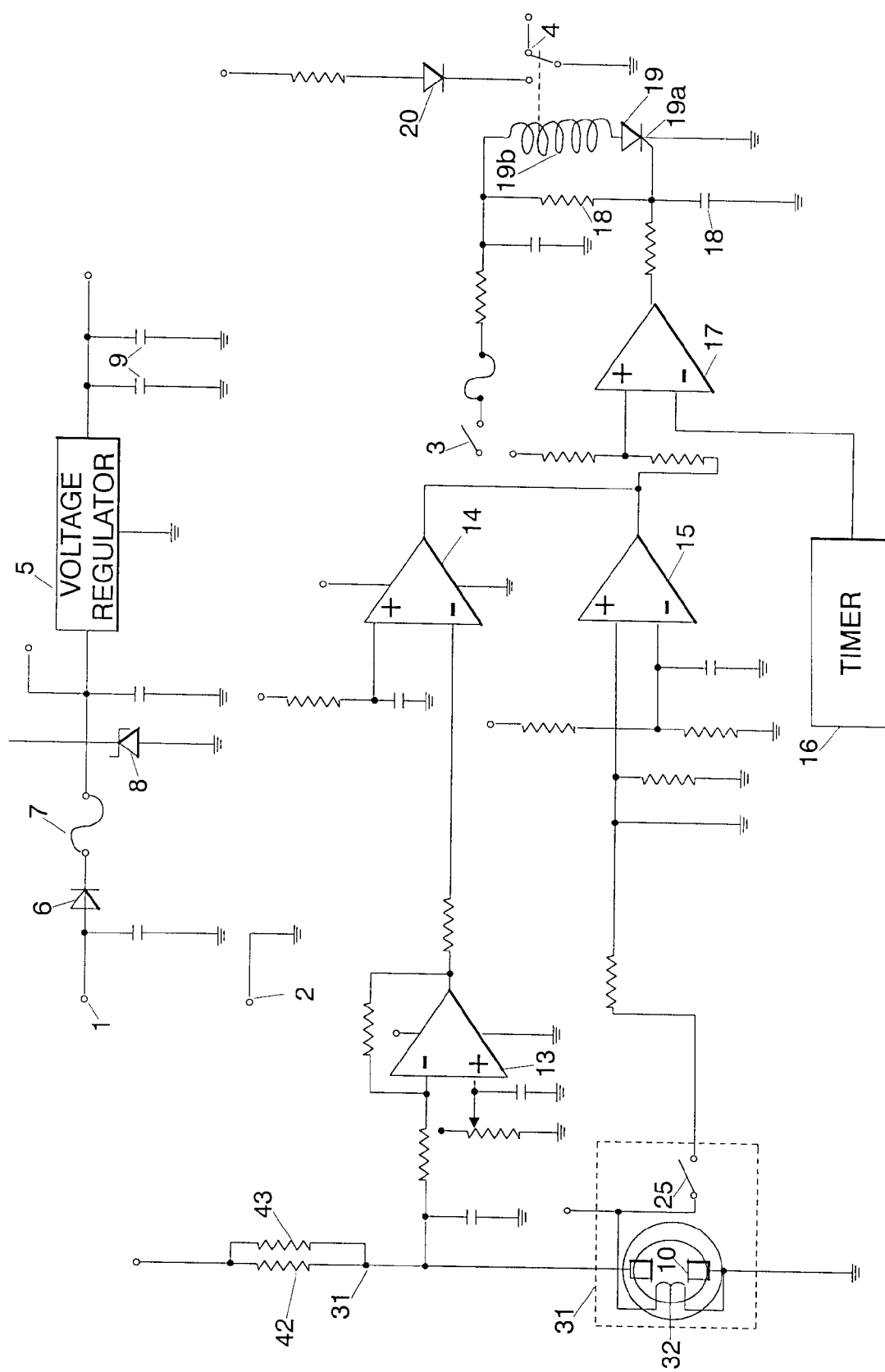
FIG. 2 is a combination circuit/block diagram of the adjunct circuitry.

An alcohol detection device in the specific form of a breathalyzer comprises a body 21 preferably formed from moulded plastic components. Body 21 is of an open-ended configuration having an inlet 22 and an outlet 23 at opposing ends to thus assist fluid flow therethrough. Inlet 22 is preferably in the form of a mouth-piece projecting from an outer casing 30 of the device to thus facilitate a user exhaling into an interior chamber 24 between inlet 22 and outlet 23. Mounted within the interior chamber 24 is an alcohol sensor 10 which is preferably in the form of an electronic semiconductor device which incorporates a heater 32 (FIG. 2). Sensor 10 preferably has an annular shaped outer body $10^a$ with sensor head $10^b$ suspended in the interior thereof. The sensor 10 is mounted substantially axially common with the longitudinal axis of chamber 24 such that the head $10^b$ of sensor 10 is disposed clear of the surrounding body 21. This exposed mounting of the head $10^b$ facilitates air circulation through the chamber 24 and thus evaporation of any condensation formed on the interior wall of the body 21. The incorporation of the sensor 10 within the circuitry is described in more detail hereinafter.

The volumetric fluid flow capacity of the chamber 24 is larger at the inlet 22 than at the sensor 10 and/or thereafter to the outlet 23. The object of providing this restrictive configuration is to provide that with a reasonable pronounced exhalation of breath at the inlet 22 a back pressure will result within that section of the interior chamber 24 between the sensor 10 and the inlet 22. This back pressure is utilized to operate a pressure sensitive switch 25 as more particularly described hereinafter.

Preferably the body 21 is formed of two components $21^a$ and $21^b$ each of a generally cylindrical configuration. Component $21^b$ has an inner end section $21^c$ adapted to fit to the associated end of component 21c and in so doing enable the mounting of sensor 10 within the interior chamber 24 in the region of the junction between the two components of the body 21. Preferably component $21^b$ substantially reduces in diameter adjacent to the junction with component $21^a$ and thereafter forms the outlet 23 of the chamber 24 in the form of a small diameter bore. This reduced size of outlet 23 together with the volumetric reduction provided by the annular shape of sensor 10 provides the desired restriction. It is envisaged that the restriction provided by the sensor 10 alone would be sufficient. By also providing that outlet 23 is of a smaller diameter reduces the surface area of the wall defining chamber 24 and thus reduces the surface on which condensation can form.

As aforesaid a pressure sensitive switch 25 is provided to be operated by back pressure in the associated section of the chamber 24. The purpose of this is to ensure that sufficient volume of exhalation breath is provided for the sensor 10 to make the measurement required of it. Unless sufficient backpressure is created in the chamber 24 switch 25 will not be operated to activate the adjunct circuitry.

As more particularly described hereinafter the circuitry also provides that switch must not only be operated but also must be maintained closed for a minimum pre-determined period of time before the circuitry will provide an adequate operating signal.

Preferably switch 25 is mounted into the interior chamber 24 between inlet 22 and sensor 10 by way of an antechamber 26. A diaphragm 27 is retained by the body 21 to sealingly separate switch 25 from the interior chamber 24 and its associated antechamber 26. Diaphragm 27 thus effectively forms part of the wall defining the interior chamber 24 and will be deflected outwardly thereof with increasing pressure therewithin. Diaphragm 27 is connected to switch 25 such as by cap 41 such that deflection of diaphragm 27 depresses switch 25.

To restrict or at least limit physical tampering with switch 25 preferably antechamber 26 is conjoined to chamber 24 by a port 28. Port 28 is dimensioned and positioned to restrict physical access via the interior chamber 24 and the antechamber 26 to diaphragm 27. In addition a suitable grid or mesh element 29 could be mounted in port 28 or otherwise between diaphragm 27 and inlet 22.

Preferably outer casing 30 is provided about body 21 to provide for further physical protection of the sensor 10 and switch 25. Casing 30 also enables fixed or detachable mounting insitu and insulates the body 21 from surrounding ambient air conditions to help stabilize the condition in which the sensor 10 operates.

Referring in particular to FIG. 2, the primary purpose of the device and its adjunct circuitry is to control an ignition circuit of a road vehicle. In FIG. 2 ignition key switch 3 and distributor points 4 represent a conventional ignition circuit of such a vehicle. In installing the device the points 4 are shorted to earth.

The circuitry is preferably powered from the automobile's battery represented by terminals 1 and 2. Preferably the circuitry incorporates a conventional stabilizing supply network comprising a voltage regulator 5 and associated protective components being diode 6, fuse 7, over voltage protection zener diode 8 and stabilizing and filtering capacitors 9. The coupling of the power supply circuit to the automobile's battery provides for a permanent supply to the circuit which is thus continuously alive.

Sensor 10 together with resistor 42 forms part of a resistive divider chain 31. Preferably a thermistor 43 and heater 32 are provided to facilitate stable and compensating temperature conditions. Sensor 10 and switch 25 have outputs to comparators 14 and 15 respectively. Preferably an inverting medium gain amplifier 13 is provided as an intermediate stage between sensor 10 and comparator 14. Comparators 14 and 15 are preferably arranged in an OR configuration with each comparator having one input thereto pre-set at a reference level. Reference voltage levels are provided t to both comparators 14, 15.

Preferably the outputs of comparators 14 and 15 provide a first input to a third comparator 17 forming an input stage to ignition circuit latching means 19.

Preferably, the arrangement is such that the latching means when set removes the short provided on the points 4. The remaining input to comparator 17 is provided by a timer 16 of conventional programmable structure. Timer 16 is programmed so that during a predetermined time period or periods comparator 17 provides an operating signal to the latching means 19 regardless of the level of the other input to comparator 17. Thus, the timer 16 can be programmed to maintain the latching state provided by the circuitry during those periods. It is envisaged that this facility will be utilized during those hours when there is a minimum likelihood of use of a vehicle being made by an intoxicated driver.

The output of comparator 17, or if the comparator 17 and the associated timer 16 are not provided, the common output of comparators 14 and 15 is connected to latching means 19 controlling the ignition circuit represented by switch 3 and distributor points 4. The latching means preferably comprises a SCR $19^a$ in series with a coil $19^a$ of a relay controlled contact wired to form the short of the distributor points 4 to earth. To reset the latching means an operating signal must be provided to the gate of (Silicon Controlled Rectifier) SCR $19^a$ to trigger the SCR and thus energise coil $19^b$. Preferably a LED 20 is provided to indicate that latching means 19 is set.

Preferably a time delay network 18 of the conventional resistive capacitor configuration is provided at the input to latching means 19. Thus an operating signal must be maintained for a period determined by the time constant of that delay network to obtain an effective operating signal to latching means 19. This ensures that not only must pressure switch 25 be operated by an exhalation pressure of a user but also switch 25 must be maintained closed for sufficient time for the capacitor of network 18 to adequately charge. Thus in using the device exhalation must not only be of adequate pressure but also for an adequate period of time for the circuitry to operate. This time delay also has the benefit that the effective measurement taken by the sensor is also after a period commensurate with the time constant of the delay circuit. This sampling delay helps provide more consistent readings as breath is essentially constant as to humidity and temperature. The sensor 10 thus tends to make the effective reading in correspondingly stabilizing conditions.

THE EYE-SENSOR COMPONENT

The eye-sensor or more particularly a scanner of an individual's retina used for the motor vehicle 10' retinal scanner 20' capable of detecting and storing, a plurality of retinal patterns for a plurality of valid drivers for a vehicle. The retinal scanner 20' is electrically connected to a vehicle's ignition system for preventing starting of the vehicle unless the retinal scanner 20' detects a retinal pattern substantially similar to one of the valid drivers. The retinal scanner 20' preferably allows up to 30 seconds for an individual to start the vehicle upon detection of the retinal pattern substantially similar to one of the valid drivers.

Figure 3:
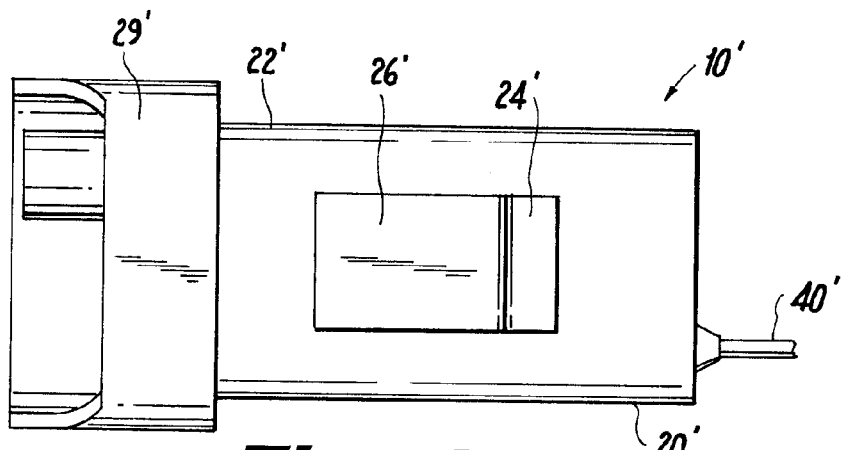
FIG. 3 is a top view of the eye-sensor component with the external housing removed to illustrate structural details thereof.
Figure 5:
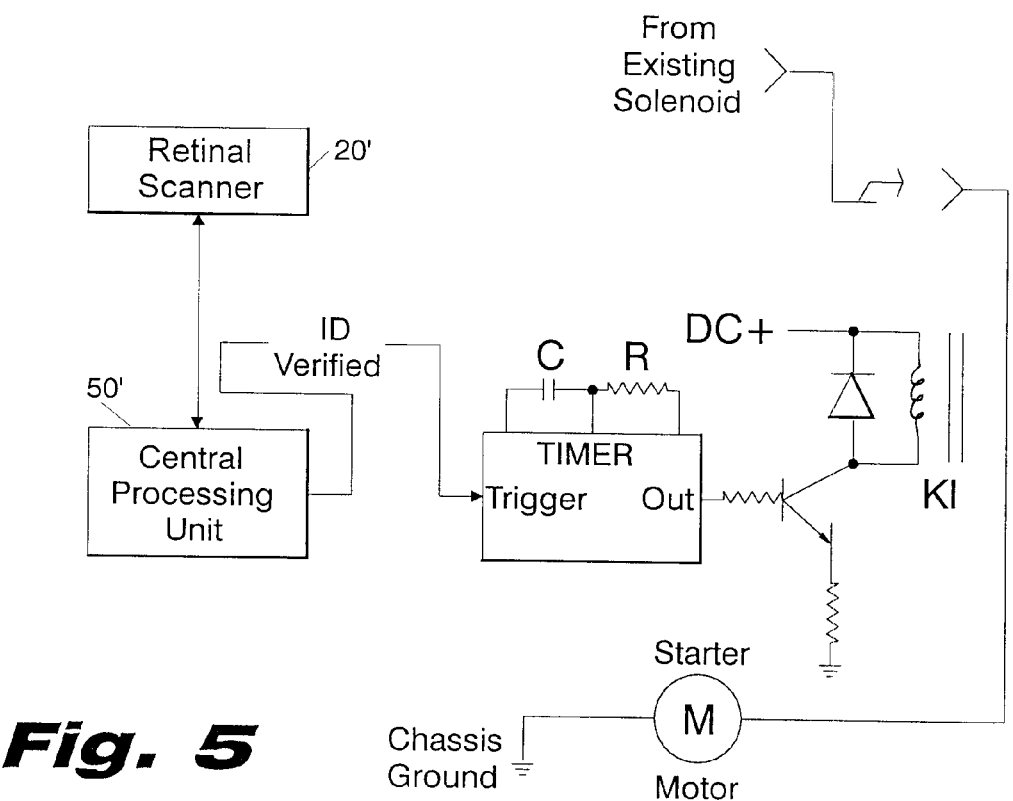
FIG. 5 is a schematic illustration of the eye-sensor.

As shown in FIGS. 3 and 5 of the drawings, the retinal scanner 20' is electrically connected to a cut-off solenoid by a coiled data cable 40'. The cut-off solenoid is electrically connected also to a starter motor's existing solenoid and the starter motor, whereby the circuit between the existing solenoid and the starter motor is closed only when the cut-off solenoid is closed. Thus, the cut-off solenoid disables the starter motor when the cut-off solenoid is open.

Figure 4:
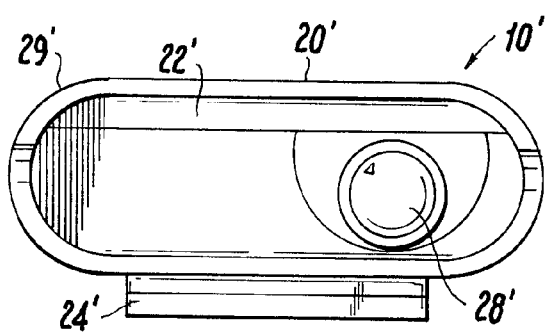
FIG. 4 is a front view of the eye-sensor.

As shown in FIGS. 3 through 5 of the drawings, the retinal scanner 20' includes an encasement 22' substantially rectangular shaped with arcuate edges. A scanning lens 28' is secured within the encasement 22' for reading the retinal pattern of the user. A central processing unit 50' is positioned within the encasement 22'. The central processing unit 50' is electrically connected to the scanning lens 28'. An EEPROM chip is electrically connected to the central processing unit 50' for storing the retinal patterns of the valid drivers. A shading member 29' is secured around a peripheral edge of the encasement 22' surrounding the scanning lens 28' for preventing contamination during scanning of the user's retinal pattern.

As shown in FIGS. 3 through 5 of the drawings, the retinal scanner 20' includes a lip 24' secured to a rear surface of the encasement 22' for removably engaging a rectangular tube 26' secured within the vehicle.

As shown in FIG. 5, the central processing unit 50' receives data from the retinal scanner, verifies the user's identification and triggers the timer unit to enable the starter motor.

In use, an individual who desires to operate the vehicle positions the scanning lens 28' near his or her eye. The scanning lens 28' reads the retinal pattern of the individual's eye. The central processing unit 50' determines if the read retinal pattern substantially matches any of the retinal patterns of valid drivers stored within the EEPROM chip. If a match is successful, the retinal scanner 20' electrically closes the cut-off solenoid for 30 seconds allowing the individual to start the vehicle for 30 seconds following the successful retinal pattern match. However, if the central processing unit 50' is unable to determine a match, then the cut-off solenoid remains open thereby preventing the individual from closing the circuit between the starter motor an the existing solenoid within the starter motor.

Figure 1:
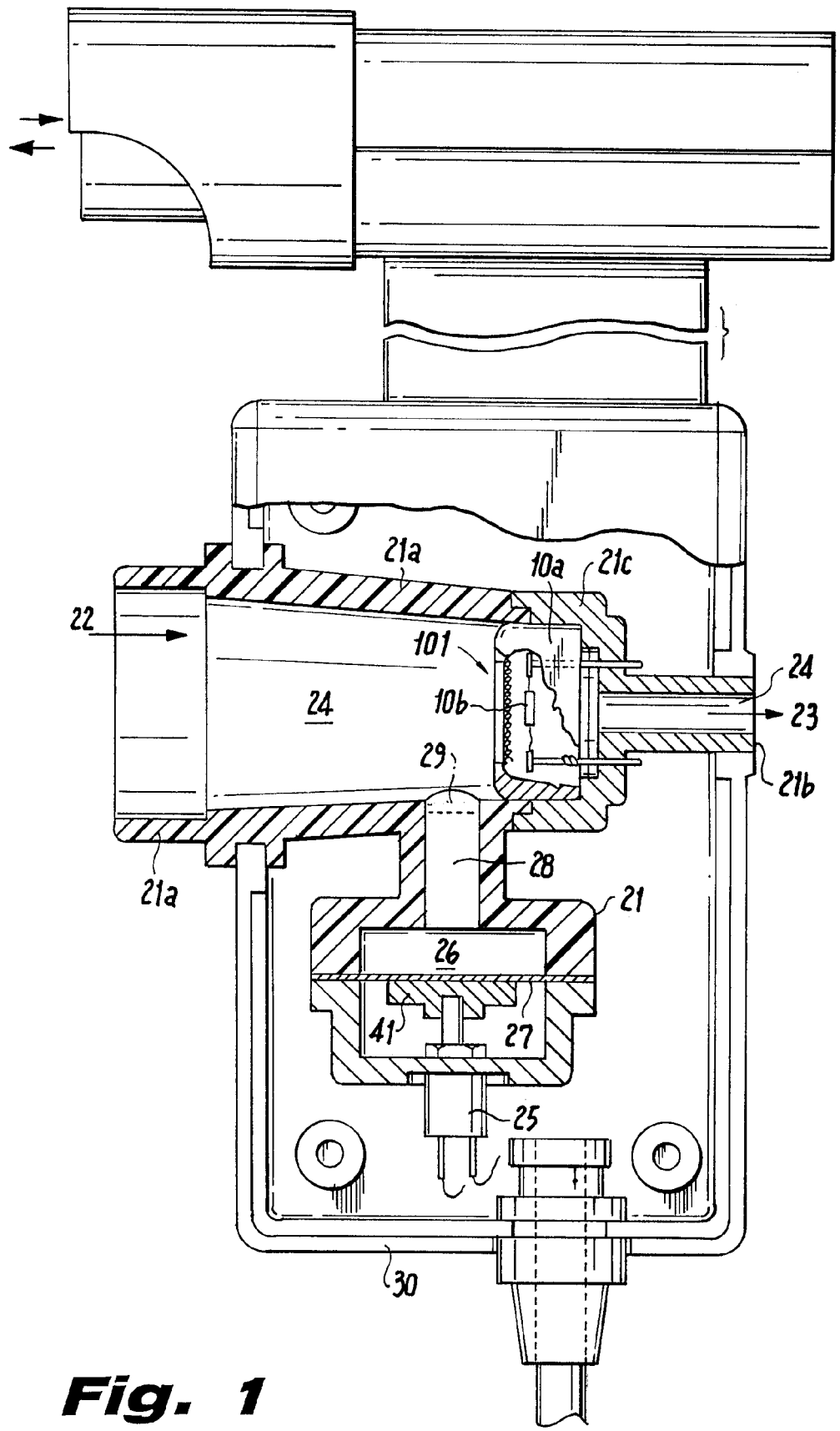
FIG. 1 is a cross-sectional view of the breathalyzer component without adjunct circuitry.

In addition, of course, to the effect on starting the vehicle imposed by the operating mode of the eye-sensor or retinal scanner 20' as just described, it will, of course, also be understood that vehicle operation or non-operation, as the case may be, is also effected by the presence or absence of alcohol in the breath of the would be driver as determined by the breathalyzer of FIGS. 1 and 2.

Figure 6:
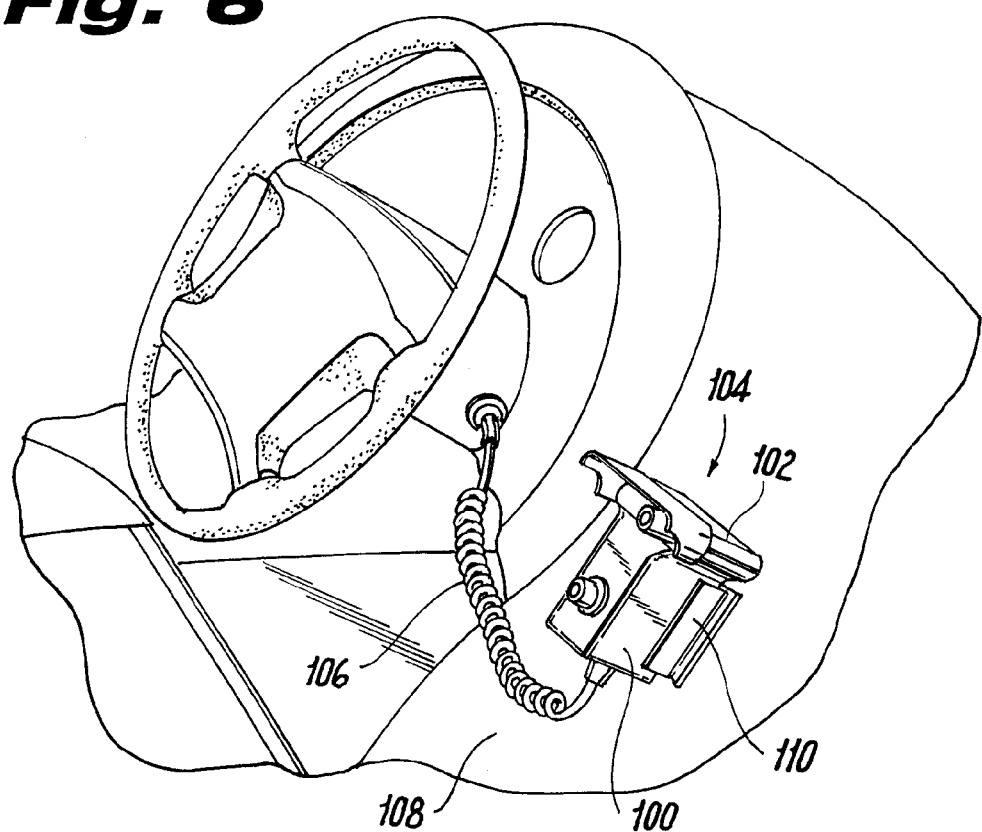
FIG. 6 is a front elevational view of a vehicle dashboard illustrating the non-use condition of the combination breathalyzer and eye-sensor.
Figure 7:
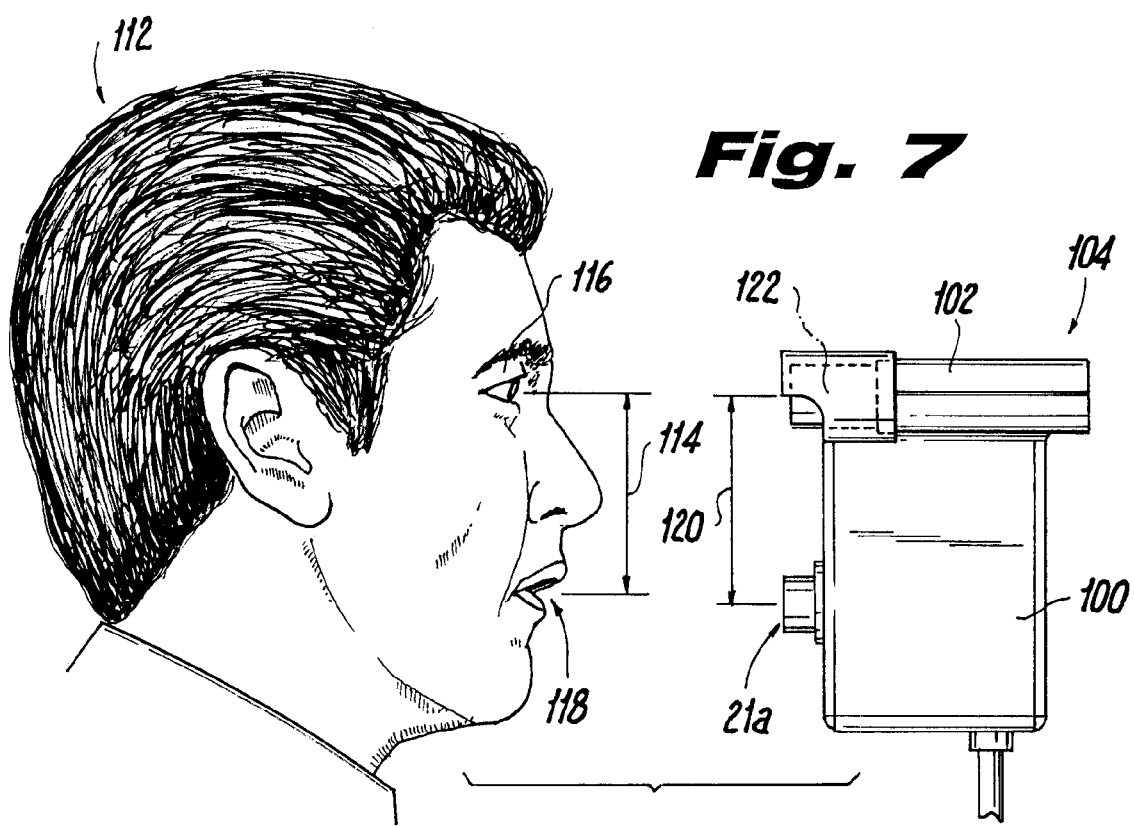
FIG. 7 is a side elevational view of the combination breathalyzer and eye-sensor in its contemplated use in accordance with the present invention.

Underlying the present invention is the recognition that in combining the FIGS. 1, 2 breathalyzer and FIGS. 3 through 5 eye-sensor in such a manner, as will be better understood in conjunction with FIGS. 6 and 7 and the description thereof which immediately follows, so that only one individual is tested both as to his/her breath and presents for identity verification his/her eyes, that the breathalyzer cannot be "tricked" using the breath of a sober passenger since said sober passenger cannot escape detection by the eye-sensor 20' as not being a valid driver.

Method of Use

In an operative combination the breathalyzer component 100 and the eye-sensor component 102 are, according to the present invention, embodied in a unitary housing 104 and have an electrical connection via a conductor 106 to the vehicle ignition. During non-use, the housing 104 preferably will be mounted in an appropriate manner on the vehicle dashboard 108, as at 110, within convenient reach of the vehicle driver 112. Incident to initial operation of the vehicle, the driver 112 will administer to him or herself a breathalyzer test and, it is also contemplated, that upon an agreed upon schedule or in response to a telephone call, a breathalyzer test will be self administered. The latter, of course, under conditions when traffic permits the vehicle to safely stop on the side of the road. Drivers tested during vehicle operation may be those taking part in a program to keep people convicted of drunken driving from taking to the road while intoxicated. More particularly, a new federal law requires that states take tougher steps against drivers repeatedly convicted of drunken driving. States, which stand to lose federal transportation money if they fail to comply, must require either complete immobilization of an offender's vehicle or the installation of an interlock system. If a vehicle is started, the interlock device of the drivers on probation periodically requires that the driver take another rolling test, to make sure the driver did not have someone else start the vehicle and is not drinking while driving. If the driver ignores the beeping sounds that the device emits when it is time for a retest, the system will cause the vehicle's lights to flash on and off. After two more minutes, the vehicle's horn starts beeping. If the driver continues to ignore the retest request, a violation is recorded in the interlock device.

With the above understanding of the conditions which might motivate a driver on probation to "trick" the test of the breathalyzer 100 using the breath of a sober passenger, underlying the present invention is the recognition that in the selection of the eye-sensor 102 and in its manner of embodiment in the unitary housing 104, that this contributes to contemporanous use of the breathalyzer 100 and of the eye-sensor 102 by only one individual, namely that of the driver 112, whose identity is verified by the eye-sensor 102.

The typical distance 114 between an individual's eyes 116 and mouth 118 is four inches plus or minus a small distance variation, and thus in the unitary housing 104, the distance 120 between the operative position of the inlet 21a to the breathalyzer 100 and the operative position of the eye-sensor 102, as at 122, in its eye-sensing relation to an individual, such as the depicted individual 112, is selected to correspond to a distance also of approximately four inches, and thus whoever is taking the breathalyzer test is positioning his or her eyes for identification-verification by the eye-sensor 102. This identification, in a well understood manner, is recorded in the administered breathalyzer test and effectively obviates the participation of two individuals, one possibly intoxicated and one sober, from thwarting the objective of a vehicle interlock system.

While the apparatus for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method for administering a breathalyzer test and verifying the identity of the individual being tested comprising the steps of arranging a breath-receiving section of a breathalyzer in an operative position adjacent a mouth of an individual, arranging an eye sensor in an operative position adjacent a pair of eyes of an individual, and arranging said breathalyzer and said eye sensor in a unitary construction and in a selected distance from each other, said selected distance being approximately the distance between an individual's eyes and mouth, to thereby contribute to contemporaneous use of said breathalyzer and of said eye-sensor by only one individual whose identity is verified by said eye sensor.

* * * * *